(12) United States Patent
Stadelmann

(10) Patent No.: US 7,422,121 B2
(45) Date of Patent: Sep. 9, 2008

(54) PROCESS FOR PRODUCING A STERILIZATION SYSTEM

(75) Inventor: Heinz W. Stadelmann, Weitbruch (FR)

(73) Assignee: PaSta Aktiengesellschaft, Vaduz (LI)

( * ) Notice: Subject to any disclaimer, the term of this patent is extended or adjusted under 35 U.S.C. 154(b) by 121 days.

(21) Appl. No.: 10/511,962

(22) PCT Filed: Apr. 17, 2003

(86) PCT No.: PCT/EP03/03917

§ 371 (c)(1),
(2), (4) Date: Oct. 19, 2004

(87) PCT Pub. No.: WO03/089377

PCT Pub. Date: Oct. 30, 2003

(65) Prior Publication Data

US 2005/0155939 A1    Jul. 21, 2005

(30) Foreign Application Priority Data

Apr. 19, 2002   (DE) ............................. 102 17 649

(51) Int. Cl.
*C02F 1/50* (2006.01)
(52) U.S. Cl. .................. 210/501; 210/192; 210/198.1; 210/209; 210/507; 210/764; 422/28; 424/404; 424/489; 424/618; 424/630; 424/649

(58) Field of Classification Search ............... 210/764
See application file for complete search history.

(56) References Cited

U.S. PATENT DOCUMENTS

| 2,344,548 | A | * | 3/1944 | Goetz ........................... 422/28 |
| 4,749,537 | A | * | 6/1988 | Gautschi et al. ............. 264/232 |
| 6,313,064 | B1 | * | 11/2001 | Miyafuji et al. ............. 502/345 |
| 6,537,730 | B1 | * | 3/2003 | Fleming et al. ............. 430/302 |
| 6,589,431 | B2 | * | 7/2003 | Nerreter et al. ............. 210/759 |

FOREIGN PATENT DOCUMENTS

| DE | 712792 | | 10/1941 |
| DE | 2307345 | | 8/1974 |
| DE | 10029082 | A1 | 1/2002 |
| JP | 408133919 | A * | 5/1996 |
| WO | WO 82/03381 | | 10/1982 |

* cited by examiner

Primary Examiner—Peter A. Hruskoci
(74) Attorney, Agent, or Firm—Kriegsman & Kriegsman

(57) ABSTRACT

The invention relates to a method for producing a sterilisation system, especially for sterilising drinking water and water for industrial use. The precious metal surface of a base material containing precious metal is initially oxidised in an acidic solution and subsequently treated in an aqueous saline solution. The invention also relates to a sterilisation system and use thereof.

12 Claims, 4 Drawing Sheets

Use examples

1. Feed: municipal water, well water or surface water
2. Outflow purified water
3. Purified water collection channel
4. Filter medium
5. Filter housing
6. Silver fabric or silver wool
7. Storage tank
8. Take-off point
9. Filter cartridge
10. Three-way tap
M. Modifier, if filter medium = reverse osmosis membrane - optional

Fig. 1

Use examples

1. Feed: municipal water, well water or surface water
2. Outflow purified water
3. Purified water collection channel
4. Filter medium
5. Filter housing
6. Silver fabric or silver wool
7. Storage tank
8. Take-off point
9. Filter cartridge
10. Three-way tap
M. Modifier, if filter medium = reverse osmosis membrane - optional

Use examples

Microbial contamination protection by silvering of the water in
- tanks.
- open systems such as air humidifiers, indoor fountains, ...
- recirculated systems (including aquarium)
- filter systems.
- hot water providers.
- water beds.
- general: closed systems.

(1) Tank system, hot water provider, reservoir, ...
(2) Silver fabric or silver wool
(3) Water-permeable vessel/bag
(4) Released silver ions
(5) Filter mat
(6) Water reservoir
(7) Blast direction aerator Example of air conditioning units/air humidifier
- direct protection of relevant components

Fig. 3     Use examples "third world"

Simplest variant

① Drawn water
③ Water-permeable container/bag
⑤ Removal of particles and pollutants
⑦ Pump with coarse filter
⑨ Water tap

② Silver fabric or silver wool
④ Tank, barrel, jar, cistern, ...
⑥ Filter cartridge
⑧ Water source: well, river, cisterns, reservoir for drawn water, lake, ...

Simple combined process for producing drinking water from surface waters, wells etc.

Fig. 4

SEM image

20 µm

PROCESS FOR PRODUCING A STERILIZATION SYSTEM

Microbiologically polluted drinking water can, on consumption, lead to serious diseases. To prevent this, drinking water is treated by appropriate physico-chemical processes. To ensure lasting protection against recontamination, chlorine, for example, is added to the treated drinking water.

If drinking water is allowed to stand over a relatively long time, or if the drinking water provided via the public mains system by the suppliers is post-treated at the point of use by active carbon filtration or by reverse osmosis for taste enhancement or for further reduction of unwanted constituents, this recontamination protection is lost by removing the chlorine present in the water. For instance it is known that the filter systems which are predominantly used in the domestic sector for drinking water post-treatment are microbially contaminated within a short time, so that, for example, the guide values of the German drinking water regulation are markedly exceeded and this water is thus unsuitable for human consumption for microbiological reasons. The same applies to drinking water charged into tanks (for example mobile homes) or for air humidifiers and air conditioning systems, where heavy microbial contamination may frequently be observed within a few days.

These microorganisms are consumed during drinking or are released together with the evaporated water. In the latter case, this can lead to what is termed humidifier fever. If biocidal active compounds are added as contamination protection, these are consumed during drinking or via respiration. This can cause serious diseases.

In closed systems such as tanks, piping systems or waterbeds, the water quality changes owing to microbiological activities which begin. The water has a musty odor and the gas development observed in waterbeds makes regular exchange of the water necessary.

Other critical items are warm water vessels, shower heads or simple floor-mounted boilers, where, owing to the elevated temperature, particularly dangerous thermotolerant microbial pollution can develop.

Hygienically safe drinking water is one of the most urgent problems of developing countries. The technologies used in the "first world" for drinking water disinfection are expensive and must be continuously serviced and monitored to ensure reliable sterilization of the drinking water and industrial water. The complex control, measuring and instrumentation technology is, in addition, only to be managed by qualified specialist personnel. These systems can only be operated cost-effectively as a central system, which assumes appropriate infrastructure. These preconditions are not met in the "third world".

For the "third world", rather sterilization processes had to be provided which ensure over long periods (years) in a maintenance-free manner a reliable sterilization of the drinking water and industrial water.

In the case of the technologies used to date, reliable sterilization is only achieved if continuous monitoring of the relevant operating parameters is carried out, at the same time permanent care by qualified specialist personnel is ensured, and a functioning infrastructure, mains grid, is available. These preconditions are not met, or are met only incompletely, in particular in the "third world" and in the domestic sector. The high costs and/or the lack of qualified personnel here argue against this.

Owing to the above-described problems, the drinking water in large parts of the "third world" is considerably microbially contaminated.

In the domestic sector ("first world"), various post-treatment units are used which are based on photochemical treatment of the water (UV disinfection) or chemical additives, for example silver compounds.

Disinfection with UV light, however, takes place only during the irradiation process itself, so that there is no lasting effect. Furthermore, irradiation with UV light leads to uncontrolled photochemical change of the water constituents, which is undesirable.

In addition to UV disinfection, various sterilization processes based on silver are also known.

WO 82/03381 describes a process for producing shaped bodies for keeping waters and aqueous solutions free from microbial contamination, in which a metal compound which is slightly soluble in water and prevents the development of microorganisms, for example AgCl, with or without support substances, is shaped at a pressure of at least 8,000 kg/cm$^2$. The metal compound is then activated by addition of readily soluble salts, by thermal treatment or chemical treatment.

Shaped bodies which are used are pressed bodies, silver compounds melted into a plastic membrane, or metal compounds melted on an inert support, for example silver wire, gold wire or platinum wire, magnesium oxide, aluminum oxide.

The desired freedom from microbial contaminations is achieved in these shaped bodies used in closed systems which release 0.1 to 1.0 mg of silver/l by a silver excess. These silver values are far above the currently permissible silver concentration of 0.01 mg/l (general value EU Directive, German drinking water regulation (TVO), or 0.08 mg/l (TVO with silver treatment)) and in part exceed even the permissible silver values in waste waters which are currently, depending on industrial purpose, 0.1, 0.5 or 0.7 mg/l.

A disadvantage with these shaped bodies is further, in addition to the complex production under pressure, the fact that these shaped bodies can only be used in closed systems and must be replenished after the system has been opened. The aluminum compounds proposed in this publication as support materials are, in addition, of concern with respect to the release of Al$^{3+}$ ions, since these can be of toxicological relevance. Also, the shaped bodies disclosed by this publication cannot be used to keep waters and aqueous solutions free from microbial contamination which contain metals less noble than silver and must be kept in the dark.

The above-described problems with exceeding the permissible silver ion concentrations, the uncontrolled release of silver ions and the requirement for replenishment, also appear in the dropwise addition of silver salt solutions known from the prior art for sterilization, or the use of silver ion-coated activated carbon or ion exchangers comprising silver ions.

DE 712 792 discloses processes for producing products of increased oligodynamic efficacy, in which etched noble metals are used for sterilization. The etching is performed under relatively mild conditions in hydrogen peroxide solution, hypochlorite solution or electrolytically at low current densities to roughen the noble metal surface. The treatment with these etching agents serves for removing organic molecules essentially adsorbed to the noble metal surface. The etched base body is then used directly for the sterilization.

DE 2 307 345 discloses using a filter body made of copper net which is in part silvered for the disinfection of water.

DE 100 29 082 further discloses a process for sterilizing drinking water and industrial water by activated noble metals in which a noble metal is etched in a first step to remove passivation layers and is then activated in a salt solution which is not described in more detail.

The object of the present invention is to provide sterilization systems which are simple to produce and are environmentally friendly and also ensure reliable sterilization of the drinking water and industrial water over long periods (years) in a maintenance-free manner directly at the point of use and to specify a process for producing and using these sterilization systems.

To produce the inventive sterilization system, the noble metal surface of a base material comprising noble metal is first oxidized in an acidic solution and, directly after or after rinsing with water, treated in an aqueous salt solution. By means of the treatment with the aqueous salt solution, depending on the type and concentration of the anions in the aqueous salt solution, slightly soluble noble metal salts or a mixture of noble metal salts of different solubility products are formed on the noble metal surface which have grown directly on the noble metal material. As a result significant advantages are achieved:

The inventive sterilization system is self-regulating, since the noble metal ions from the surface released to the water during the sterilization are replenished directly from the core material.

No boundary layer exists between core material and noble metal salt surface. The renewal of consumed noble metal ions from the core material is thus not kinetically inhibited, so that a sufficiently rapid replenishment is ensured by the redox system noble metal/noble metal ion. The oxygen required for the oxidation can, owing to the microporous amorphous surface, diffuse unhindered to the $Ag/Ag^+$ interface.

The noble metal salt surface area is extremely large and has, with amorphous and crystalline areas, regions of different activity. The crystalline and amorphous noble metal salts are in direct contact with one another and in direct contact with the bare silver surface, so that, overall, the following regions of differing redox activity and solubility form:
  i) pure silver surface accessible via pores of the amorphous layer,
  ii) amorphous noble metal salt layer,
  iii) crystalline noble metal salt layer,
  iv) contact zone silver-amorphous noble metal salt layer,
  v) contact zone silver-crystalline noble metal salt layer and
  vi) contact zone amorphous noble metal salt layer-crystalline noble metal salt layer,
  vii) contact zone silver-amorphous noble metal salt layer-crystalline noble metal salt layer, that is to say one-, two- or three-phase zones, the ratio of which may be controlled by the production conditions.

When the inventive sterilization system is present in the water to be sterilized, an equilibrium is established between noble metal ions in the water and on the surface. The dissolved ions exert a "pressure" on the ions of the surface and thus prevent these likewise going into solution. In the case of the removal of water and the generally resultant inflow of fresh water in the open system, the noble metal ion concentration changes and thus the "pressure" on the ions of the surface. These pass into solution until the original concentration is reestablished. The losses of noble metal ions at the surface are compensated for by the noble metal base material.

As a result of the redox system noble metal/noble metal salt (not kinetically inhibited), the system, even when silver salts are used, is insensitive to illumination and metal ions of lower nobility as the relevant noble metal salt.

As base material, use can be made of noble metals or silver-, copper- and gold-based noble metal alloy in the form of solid bodies, wires, metal wools, woven or knitted wires or noble metal wire/plastic mixed fabric and/or noble metal wire/carbon fiber mixed fabric or supports coated with these noble metals, noble metal powders, shaped bodies comprising noble metal powders and also coatings comprising noble metal powders.

The use of silver as noble metal has proved to be particularly suitable.

It is additionally possible to use noble metal powders as base material. The noble metal powders, in particular silver powder, can have particle sizes from the nanometer range up to the particle size range of powder coatings, preference is given to particle sizes in the range of from about 1 to 500 μm, particularly preferably of from about 10 to 90 μm.

The noble metal surface is oxidized in an acidic solution preferably comprising water. Preferably, the oxidation solution comprises oxidizing inorganic or organic acids and/or mixtures of oxidizing inorganic or organic acids.

Preferably, the acids contain sulfur in oxidation state +6, nitrogen in oxidation state +5, the halogens chlorine, bromine and iodine in oxidation state +5 or +7, boron in oxidation state +3 and/or oxygen in oxidation state −1 or −2.

It is also possible to use aqueous solutions containing water-soluble strongly oxidizing substances and acids.

The pH of the oxidation solution should preferably be less than 1.

The chemical composition of the acidic oxidation solution and the oxidation conditions depend on the type of noble metals used. Depending on the respective oxidizing agent, the desired oxidation of the noble metal can be achieved as soon as at room temperature. The acids or oxidizing agents are preferably used in a concentration between 0.1% by weight and a concentrated solution, particularly preferably in a 25 to 30% by weight solution in the case of noble metal wires and 10 to 18% by weight in the case of noble metal powders.

By means of the oxidation of the noble metal surface, not only is the elemental noble metal surface converted with formation of positively charged noble metal ions, but passivation layers and organic impurities are also removed.

Counterions of the noble metal ions on the surface which are used are firstly essentially the anions of the acids, or the oxoanions of the oxidizing agents. These counterions are then replaced by the anions of the salt solution in accordance with the composition of the salt bath and any preceding rinsing with water with the formation of slightly soluble noble metal salts or a mixture of noble metal salts of different solubility products.

To limit the oxidation of the noble metal to the surface area, to avoid noble metal losses and to attain mechanical stability, the residence time in the oxidation bath is restricted to a few seconds to minutes. It has proved to be advantageous then to interrupt the oxidation process abruptly by immersion or rinsing with neutral tap water free from oxidizing agent at room temperature. By means of the rinsing or immersion in tap water, not only is the oxidation interrupted, but the readily soluble noble metal salts formed by the oxidation are also at least partly converted into noble metal hydroxides, noble metal oxides and/or noble metal carbonates by the hydroxide and carbonate ions present in the tap water. Costs connected with the contamination of the salt solution by carryover of the oxidation solution are also avoided.

After the rinsing with tap water, or directly after the treatment of the base material in the oxidizing agent, the base material oxidized at the noble metal surface is immersed in a salt solution.

The salt solution can contain various anions. Preferably, the anions of the salt solution are selected from the group of chlorides, bromides, iodides, carbonates, hydroxides, phosphates, sulfates, acetates, borates, tetraborates, perborates, chlorates, perchlorates, citrates, fluorides, iodates, paraperiodates, bromates, perbromates, permanganates, percarbonates, persulfates, oxalates and/or tartrates, particular preference being given to salt solutions which comprise chlorides and/or bromides. By means of the type and concentration ratios of the relevant anions in the salt solution, the kinetics and thermodynamic properties of the sterilization system can be adapted to the properties of the water to be sterilized and its water hardness. For sterilizing water from osmosis plants, it has, for example, proved to be advantageous to use bromide-containing salt solutions.

It is equally possible to use those anions which lead to the formation of pharmacologically active silver compounds, for example silver sulfadiazine.

As a result of the treatment of the oxidized noble metal surface with the salt solution, a highly porous amorphous noble metal salt layer in the subu range is formed directly on the elemental silver wire surface, from which, inhomogeneously distributed crystalline regions extending down to the silver wire grow.

As cations in the salt solution, use can be made of, for example, alkali metal cations or alkaline earth metal cations. The use of ammonium compounds as cations and sulfide ions as anions should be avoided not only in the salt solution but also in the oxidation solution, since these complex or block the noble metal ions.

The residence time in the salt bath is a few minutes to some days.

To achieve rapid formation of the desired slightly soluble noble metal salts or mixture of noble metal salts having various solubility products on the surface, it is advisable to provide the desired anions in the salt solution at high concentrations, that is to say to use readily water-soluble salts at high concentration, if appropriate even in saturated solution. At all events, the total salt concentration should be at least 0.1% by weight. After the system has been removed from the salt bath, it is ready for use for sterilization.

Preferably, the treatment in the acidic solution should follow the quenching with tap water and/or the treatment in the salt solution at a temperature between 10° and 130° C., preferably at below 80° C., and particularly preferably at 20° C.±5° C.

By means of the inventive treatment of the noble metals or noble metal ion-surface, the respective equilibrium concentration forms spontaneously in the water to be sterilized via the interaction of the noble metal salts on the surface and the counterions present in the water. The sterilization system is thus self-regulating.

Via the chemical composition of the surface, that is to say via the respective proportion of the noble metal compounds of different slight solubility on the surface, furthermore, the amount of noble metal released as a maximum may be adjusted, so that the applicable limit values can be reliably maintained. The sterilization system may thus be adapted to different water qualities and limit values.

The support material does not only perform mechanical tasks. It is rather also an active compound depot. Owing to the high amount of noble metal in the bulk, in this manner service lives of a plurality of years with retained activity may be achieved without problem, so that a long-term slow-release action is achieved.

By means of the fact that the inventive system provides the redox pair noble metal/noble metal ion, in particular $Ag/Ag^+$, with the noble metal, in particular silver, in excess, the system is largely insensitive to oxidizing or reducing substances and to illumination.

Generally, the temperature of the acidic solution, the salt solution and the tap water during the treatment is between 10° C. and 130° C., preferably at most 80° C., and particularly preferably 20° C.±5° C.

In a first preferred embodiment, the base material used is a knitted fabric, knitwear or woven fabric of noble metal fibers together with carbon fibers or synthetic fibers. The noble metal-synthetic-woven fabric, -knitted fabric or -knitwear is, after the knitting or weaving process, thermally converted into carbon. These noble metal/carbon base materials act not only in an antimicrobial manner, but also by adsorption. Thus it is possible, simultaneously also to adsorb toxins, or, by using different types of functional fibers, to incorporate further properties, for example sensory properties, into the sterilization system. For example, such functional fibers could be especially coated synthetic fibers which react to biological or chemical characteristics, such as immunoassays.

The inventive knitted fabrics, knitwear or woven fabrics can be used not only for sterilizing drinking water and industrial water, but, for example, also in functional textiles, dressing materials, filter fabrics, as germ barrier, in domestic hygiene or in ion generators, in cooling lubricants or environmental technology.

The inventively treated silver wires or threads can, in a further embodiment, also be used in the form of a plait, for example in Perlator aerators, for protecting surfaces, for germ barriers or in ion generators.

A great multitude of possible applications result from using the inventively treated noble metal powders, in particular the treated silver powders.

These powders can be processed, for example, in processes known from plastics engineering, surface engineering or powder technology:

Thus it is possible, for example, to embed the inventively treated noble metal powders into a plastics matrix (blends, co-extrusion, co-lamination). Also, the inventive powders can be used for coating surfaces, for example to protect the material, for sterilization or keeping it free from germs. The coating can be performed, for example, by dipping, spraying or powder-coating.

The inventively treated powders can be formed as such or as a mixture with metallic powders or nonmetallic powders to provide a porous antimicrobial shaped body. Nonmetallic powders which can be used are, for example, activated carbon, zeolites, silica gel etc. The shaping can be performed using known pressing processes, such as CIP or HIP or slip casting.

The inventive powder coatings can be used, for example, on working surfaces, cutting boards, camping tableware, domestic appliances etc. Inlet and outlet air tubes in air conditioning and ventilation plants which are preferably powder coated can also be kept free from germs by the inventive surface coating. Germ formation in these systems generally results from the formation of water of condensation.

Further potential uses are films, for example food films, or food packaging, which are covered with a sheet of the inventively treated powder, for example by co-extrusion or lamination.

Wires, yarns or threads, but also foams, may also be coated or impregnated with the inventively treated powder, for example by co-extrusion or dipping. The coated threads give, compared with the inventive fabric according to the first preferred embodiment, an improved support comfort, or an improved dosage of the required amount of silver, in particular for short-term uses.

In principle it is possible to coat all conceivable shapes and materials with the inventively treated noble metal powder, in particular by dipping. For instance, bandages, diapers, sanitary towels, can be soaked or impregnated with a suspension comprising the inventively treated noble metal powders. Also, sintered bodies comprising inventively treated noble metal powders can be provided.

For open, weeping or burn wounds, for example vapor-permeable films made of fluorocarbon materials or other materials which do not stick to the wound can be antiseptically coated with the inventively coated noble metal powder.

The porous shaped bodies made of the inventively treated powder or the powders having additives of metal or nonmetal powders can be used in Perlator aerators or as metal filters. Use in antifouling coatings, wood protection paints and antimold paints is also possible. From the further application sector of medical technology, only the following will be mentioned by way of example: the surface coatings of medical instruments, such as catheters, infusion needles, surfaces coming into contact with blood (hemodialysis) which can be equipped so as to be antimicrobial using the inventively treated base material in the form of powders or wires.

Using the inventive sterilization system it is possible to sterilize reliably drinking water and industrial water and other water-based systems with low expenditure, or to protect them in a lasting manner against recontamination. By means of the inventive surface properties, only minimal noble metal, in particular silver, ion concentrations are required. The relevant guide values are thus maintained reliably. These low concentrations, but sufficient for reliable activity, are set automatically via establishment of chemical equilibrium. The absolute amount of material used determines the service life which is markedly above one to a plurality of years. Owing to the self-regulation and renewal, the use of control, measuring and instrumentation technology can be dispensed with.

The inventive sterilization system can be introduced into the water circuit at any desired point. Various typical applications of the inventive sterilization system are shown in the following FIGS. 1 to 3. In the figures.

The material itself is located either in separate cartridges which are integrated into the line via conventional connection techniques, or it is located directly in the filters or the tanks. The base material used is, depending on the planned use, preferably silver wire, silver wool, or a synthetic fabric interwoven with silver wire.

Figure 1A:
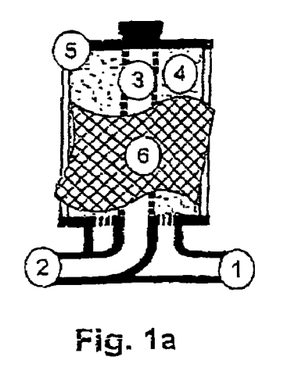
FIG. 1 shows a diagrammatic representation of domestic systems and water filters having the inventive sterilization system.

This inventive sterilization system can be used, for example, in domestic systems for post-treatment of municipal water, for sterilizing air humidifiers, hot water systems and tank systems, or closed systems for decentralized drinking water disinfection in the "third world", but also in medical technology, or for preserving water-based emulsions or dispersions, or in the field of domestic hygiene and food hygiene:

a) Use of Surface-treated Silver/Synthetic Fabric or Silver Wools in Domestic Systems for Post-treatment of Municipal Water Activated carbon filters or what are termed reverse osmosis systems for the domestic sector remove, owing to their principle of action, the chlorine used as protection against recontamination. This leads to the filters being colonized in a short time by microorganisms, which lead to serious bacteriological pollution of the drinking water. To prevent this, an inventive sterilization system, for example silver fabric or silver wool or silver/synthetic fabric, can be wound around the filter medium (4) (filter membrane (reverse osmosis), for example the filter block (pressed activated-carbon blocks)), which prevents direct colonization of the filter media (FIG. 1a). Alternatively, the sterilization system can be introduced directly into the product water collection line (3) in FIG. 1b (reverse osmosis, activated carbon, not only pressed blocks, but also granules). Water thus treated is germ-free and, owing to the dissolved noble metal ions, is protected from recontamination.

Figure 1B:
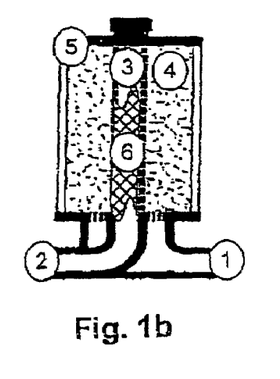
Figure 1C:
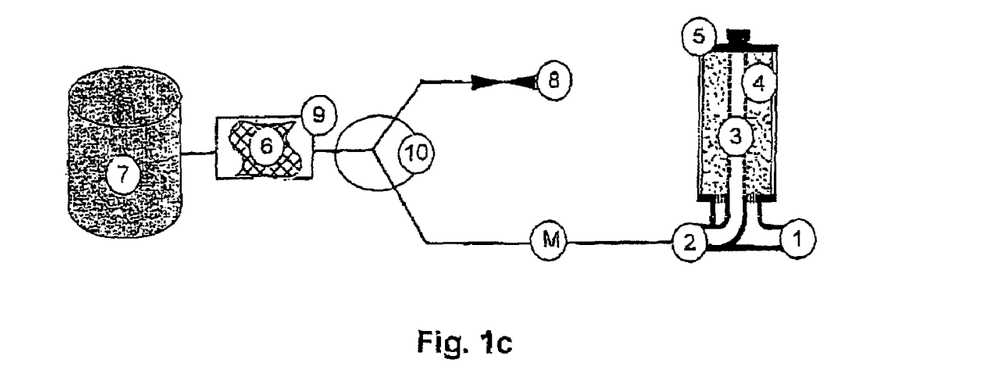

In systems having an intermediate storage tank (7), it is advantageous to connect the sterilization system between tank (7) and three-way tap (10), as is shown in FIG. 1c.

Depending on the initial pollution and the general situations, the possible methods can be combined. Generally, however, one of the three possible methods is sufficient to ensure sufficient protection in the case of municipal water post-treatment systems or in the case of well water. In systems without a tank, in particular the variants shown in FIGS. 1a, b are used, while in systems having a tank, preferably the variant shown in FIG. 1c, or a combination thereof is used.

b) Use of Surface-treated Silver/Synthetic Fabric, or Silver Wools, in Air Humidifiers, Hot Water Systems and Tank Systems, or in Closed Systems In the use examples shown in FIGS. 2a and b, the inventive sterilization system is used predominantly in closed systems (FIG. 2a) or in semi-closed systems such as storage tanks (batch operation), with it preferably being introduced directly into the tank.

Figure 2:
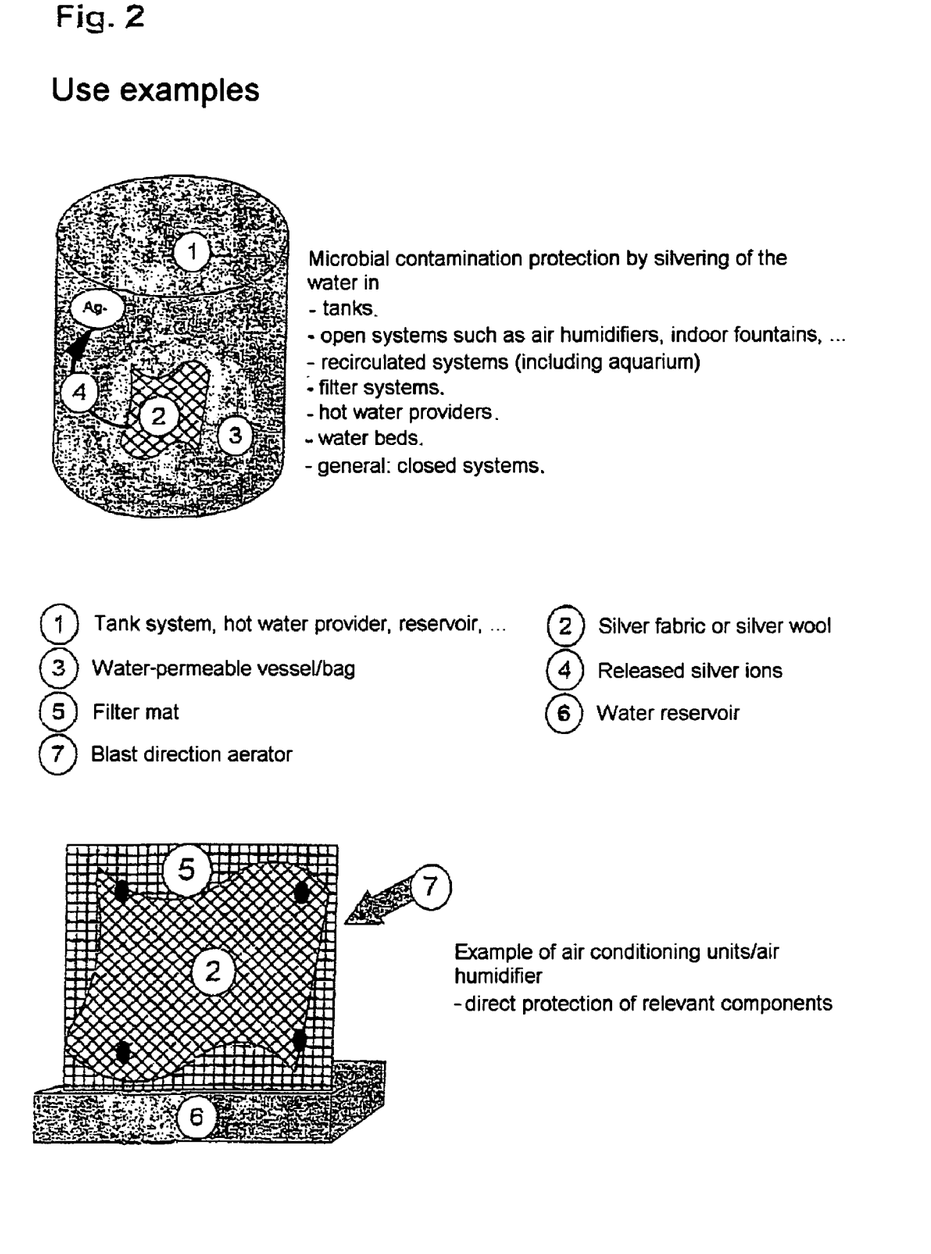
FIG. 2 shows use examples in a closed system and a semi-closed system and FIG. 3 shows use examples for the "third world".

In air humidifiers, air conditioning systems, hot water tanks or floor-mounted boilers, water tanks (camping) or in waterbeds, with time heavy growth of microorganisms is observed. This leads to health hazards (air humidifiers, water tanks etc.) or to an increased maintenance requirement (exchange of water in waterbeds, because gas bubbles form owing to microbiological activities). This can be prevented by using the inventive system with silver/synthetic fabric as base material, or by using an inventive system having silver wool as base material (FIG. 2). In this case the silver-based materials can be introduced either directly or in water-permeable housings (FIG. 2a). In corresponding air humidifier types, the inventive system based on silver/synthetic fabric can also be placed directly onto the filter mats (5) in FIG. 2b. For protection against Legionella, treated Cu threads can be additionally interwoven.

c) Use of Surface-treated Silver/Synthetic Fabric or Silver Wools for Decentralized Drinking Water Disinfection—"Third World"

Figure 3:
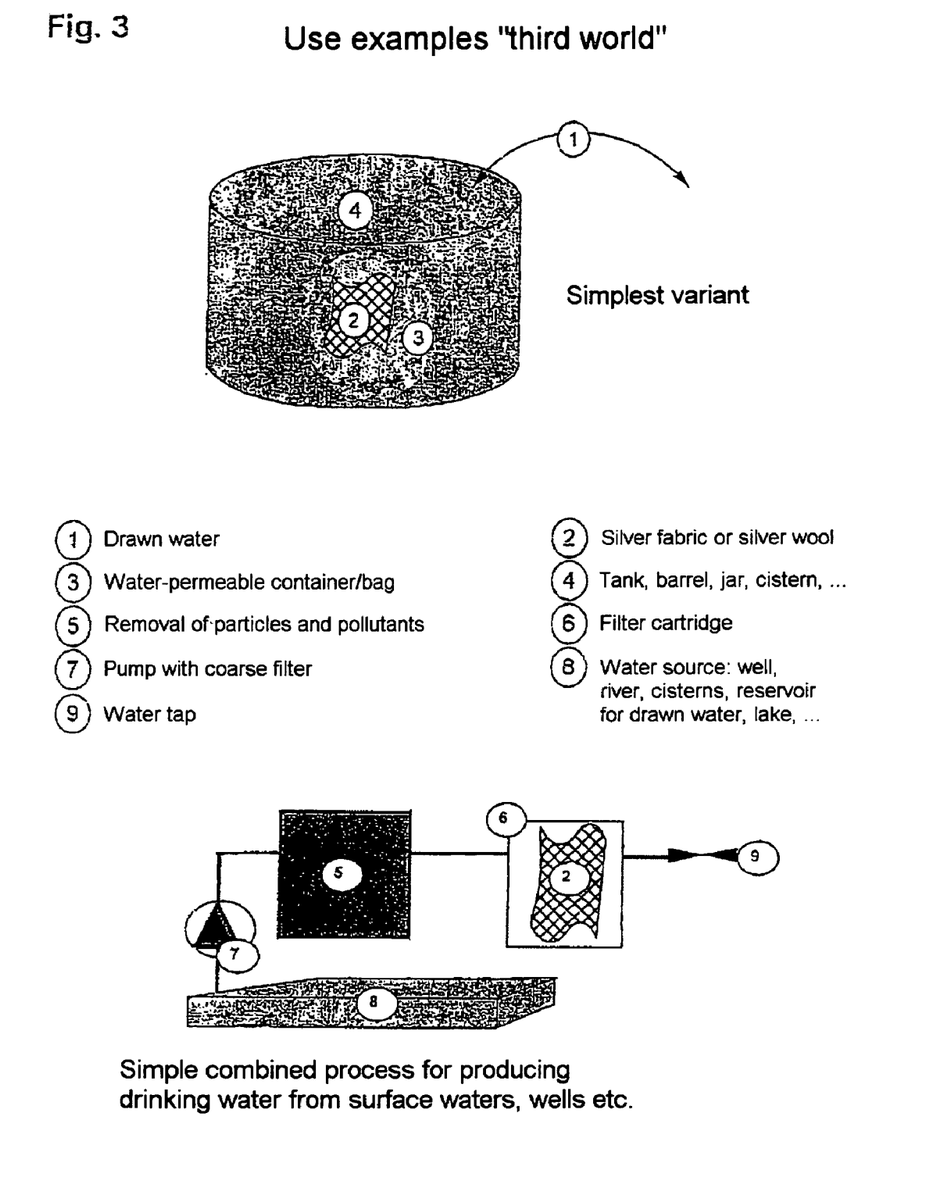

Hygienically safe drinking water is available only with restrictions in the "third world". In view of lacking infrastructures, simple decentralized drinking water treatment must be provided. Inventively treated silver/synthetic fabrics or silver wools can be used advantageously for this. In the simplest case, for this, the inventively treated silver/synthetic fabric or silver wool is placed into the appropriately equipped storage vessel—water vessel—and the vessels are then filled with the drawn well water or river water (FIG. 3 "simplest variant"). At appropriate times of action of the sterilization system, even highly microbially polluted water can be sterilized. Thus the inventive sterilization systems are suitable not only for preventing recontamination, but also for treating drinking water.

In simple cases, it is sufficient to store for several hours drawn surface water or well water in bottles, canisters or other vessels.

If rainwater is collected in cisterns, an appropriately treated amount of silver/synthetic fabric, or silver wool, can be introduced into the cistern or the outlet (where present) (FIG. 3).

Drinking water disinfection using the inventively treated silver/synthetic fabrics, or silver wools, can be combined with other technologies. Thus this technique, together with a water pump and a simple filter system, for example a combination of sand filter and activated-carbon filter, is a complete, simple to handle, water treatment system (FIG. 3 "simple combined process"). Depending on the technical circumstances, other combinations can be implemented.

d) Use of Surface-treated Silver/Synthetic Fabric in Medical Technology

Silver, owing to its antibacterial activity, can also be used in many areas of medicine. The inventive systems using silver/synthetic fabrics as base material, which can also have elastic properties by using corresponding threads, may also be used advantageously in the following areas:

1. In a similar manner to fabric tubes, the antimicrobially active silver/synthetic fabric can be used in dialysis tubes, catheters, plastic canulas, infusion tubes, injection ports, microsurgical instruments, probes etc. as microbial protection.
2. Antiseptic coating on doors, telephones, valves (infusion drop flow regulation) etc.
3. Glove fabric or face mask inserts for preventing carryover of germs by personnel, or as infection protection for the personnel.
4. Wound dressings; compresses, plasters etc. if required, in combination with activated carbon (for example smelling, open wounds, or activated carbon as store for slow release of medicaments previously absorbed to the activated carbon), use of silver-carbon fiber-fabric.
5. As sterile indicating probes suitable for long term use, in combination with sensor threads (for example immunoassay principle).

e) Use of Surface-treated Silver/Synthetic Fabric for Preserving Water-based Emulsions and Dispersions Water-based cooling lubricants or solvent-free water-based paints are rapidly decomposed by microorganisms. Therefore, preservatives must be added to these. These biocidal substances can trigger allergies in direct skin contact, as aerosol or gaseous, or trigger other health concerns. Furthermore, in the case of cooling lubricants, constant monitoring and replenishment are necessary, and in the regular exchange of these cooling lubricants, cost-intensive waste waters are produced.

By using the above silver/synthetic fabrics, it is possible to keep water-based emulsions or dispersions germ-free for a long time. For instance, in the case of the permanent recirculated cooling lubricants, it is sufficient to introduce a filter covered with this fabric into the circulation. In the case of dispersions charged into vessels, for example wall paints, distilled water is to be used which has been previously treated with these silver/synthetic fabrics. In supplementation, a thin reusable fleece of this fabric can be placed onto the surface of the dispersion. This serves as additional germ barrier against the penetration of bacteria via the lid opening.

f) Use of Surface-treated Silver/Synthetic Fabric, or Silver Wools, in the Domestic and Food Sectors In the processing and handling of foods, in kitchens and in the home, inventively produced silver/synthetic fabrics can be used to maintain the required hygiene. They can protect working surfaces and floors over a large area and, introduced into the bottoms of thawing vessels, can reduce the salmonella hazard existing during the thawing of poultry. Introduced into gloves they reduce the transfer or carryover of germs.

They can further act as long-term hygiene filter and sieve material, and in brushes (including toothbrushes), sponges, cleaning cloths etc, they can prevent or reduce colonization by harmful microorganisms and, as inlays in shoes or in the underarm or pubic region they can control odor formation of microbial origin.

Furthermore, by fabric applied on the surface, for example walls (directly under wallpaper) and flower pots (directly to the soil) and also other goods or foods to be protected from moisture-related mold infestation, can be protected by simple covering.

g) Use of Surface-treated Silver Powders

As explained above, surface-treated noble metal powders, in particular silver powders, can be used for coating a multiplicity of surfaces. The inventively treated powders can also be embedded in plastic matrices, or can be processed in the known processes of powder technology, in order to provide antimicrobially active articles.

The invention will be described below with reference to examples.

1. Example

Production of a Sterilization System from Silver Wire

A silver wire having a diameter of 0.05 to 0.5 mm is first rolled flat to increase the surface area. It is then treated for about three to five seconds in an acidic aqueous solution which comprises, as acid, a compound containing nitrogen in oxidation state +5 and/or sulfur in oxidation state +6 and/or oxygen in oxidation state −1, rinsed with tap water and stored overnight in a solution comprising $Cl^-$ and/or $Br^-$.

The sterilization system can also be produced in a continuous process. In this case silver wire, if appropriate rolled flat, which is located on a spool is unwound continuously and passed through the acidic aqueous solution for approximately three to five seconds, preferably a concentrated solution of an oxo acid of main group elements V-VII of the second and third period, in their highest oxidation state.

In a further bath containing tap water, the oxidized silver wire is "quenched" and then transferred to a salt solution.

2. Example

Production of a Sterilization System from a Silver/Polypropylene Fabric

A fabric of polypropylene threads together with silver threads is treated for approximately 3 to 5 seconds in the acidic solution and then in tap water and the salt solution in accordance with Example 1, as a result of which the surface of the silver threads is essentially oxidized. A portion of the $Ag^+$ ions is infiltrated into the polypropylene, so that in this system, in addition to the $Ag^+$ ions on the silver surface, readily available $Ag^{30}$ ions are also available in the PP fabric and the actively sterilizing surface is increased in comparison with pure silver wire.

3. Example

Production of a Sterilization System Having Carbon Fiber/Silver Fabric

A synthetic fiber/silver wire mixed fabric is thermally converted to a carbon fiber/silver wire mixed fabric. Then a procedure in accordance with Example 1 is followed.

4. Example

Production of a Sterilization System from Treated Silver Powder

Instead of the silver wire in accordance with Example 1, commercial Ag powder is used which is first deagglomerated and is then placed in the acidic aqueous solution for in the region of from seconds to minutes. Then it is separated off, washed and the washed powder stored overnight in the solution comprising $Cl^-$ and/or $Br^-$.

5. SEM Image of the Surface of a Sterilization System

Figure 4:
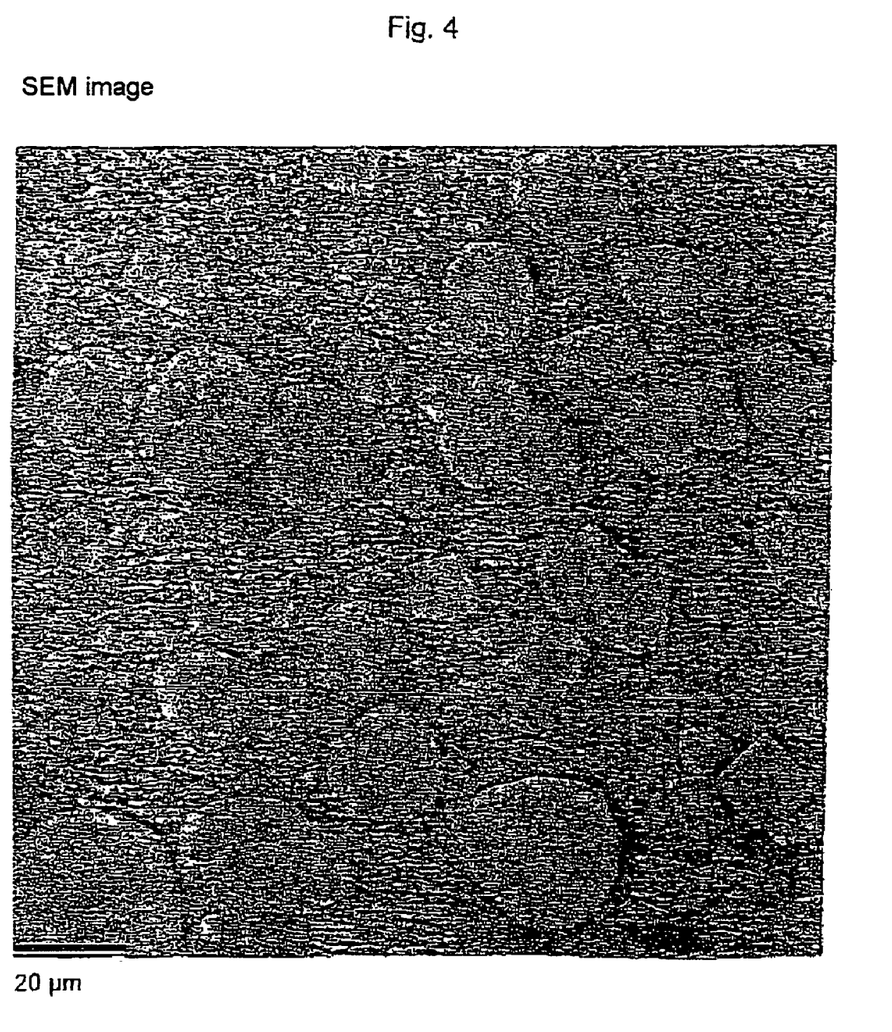
FIG. 4 shows an image of a silver surface of the sterilization system.

To study the silver surface by means of SEM imaging, from a sterilization system produced in accordance with Example 2 (polypropylene/silver thread; salt bath: NaCl solution), polypropylene was removed and the remaining silver thread having the oxidized surface was studied. The SEM image is shown in FIG. 4. The bar in the lower region of the SEM image is equivalent to 20 µm.

The image shows a thin amorphous and porous surface layer, the thickness of which may be presumed to be in the submicrometer range. The dark areas under the amorphous surface layer may be the bare silver wire. The SEM image further shows crystalline silver compounds (for example $AgCl$, $Ag_2CO_3$ etc.) on the surface.

The inventive sterilization system is therefore distinguished by a heterogeneous extremely large surface, and areas of different activity are present (amorphous and crystalline areas). The redox activities of the amorphous and crystalline surface regions which are in direct contact with the bare silver surface are likewise different. By this means, overall, the establishment of equilibrium may be controlled (kinetics), and also the equilibrium concentration itself (thermodynamics).

6. Tests Under Conditions of Practice

I. Activated-carbon Filter

Test object: A sterilization system based on carbon fiber/silver fabric produced in accordance with Example 3 was situated in the product water collection channel (FIG. 1b). After a standing time of four weeks, a sample of the stagnant water situated in the take-off line was studied and also, after initial running, filtered water. The test results are shown in the table below:

| Parameter | Stagnant water | Filtered water | Feed water |
| --- | --- | --- | --- |
| Colony count | 165/62 | 0/0 | 0/0 |
| Silver content | 0.007 mg/l | 0.005 mg/l | <0.001 mg/l |

The guide values for the filtered water are met. (If the filter had not been protected, then it would have been colonized by microorganisms and thus the water after initial running would also have been contaminated).

The contamination protection prevented, as would otherwise be customary, microorganisms from penetrating via the take-off line and being able to colonize the filter.

II. Reverse Osmosis Systems

Test object: Domestic osmosis system with tank, microbially contaminated in operation. The osmosis water produced was unfit for human consumption. After introducing the contamination protection (see FIG. 1c, Example 1), the bacteriological findings corresponded to the requirements of the German drinking water regulation.

| Parameter | Without inventive sterilization system | With inventive sterilization system |
| --- | --- | --- |
| Colony count (20° C.) | >2000 | 10 |
| Colony count (36° C.) | >500 | 20 |
| Coliforms | positive | negative |
| Escherichia coli | positive | negative |
| Result | all limit values exceeded | all limit values met |

With osmosis water, the silver concentration, as a result of the system, is higher than in the case of municipal water only filtered over activated carbon. The values are in part above the general limit value of 0.01 mg/l, but still below the limit value of 0.08 mg/l for silver-treated drinking water. The silver concentration may, if desired, be reduced by intermediate connection of a "modulator", or by varying the composition of the salt bath, to the values as listed in Example I.

The test user equipped a plurality of osmosis systems which were continuously monitored, for example by health officials. Up to the end of the test time period, that is to say after over four years of use, no diminution in activity was observed in any of the monitored systems. In this time, no maintenance work or even material exchange took place.

Thus the tests under conditions of practice show that, using the inventive sterilization system, reliable long-term protection against microbial contamination in drinking water plants etc. can be arranged. At the same time, the results prove that using these materials, not only recontamination protection can be arranged, but also highly bacteriologically contaminated water can be sterilized without problems and the requirements of the German drinking water regulation can be met, including with respect to contamination of the drinking water with silver ions. Thus the inventive sterilization system can also be used for drinking water treatment of bacteriologically polluted surface waters, wells etc.

The invention claimed is:

1. A process for producing a self-regulating sterilization system adapted for subsequent maintenance-free sterilization, said process comprising the steps of:
   (a) oxidizing a noble metal surface of a base material comprising noble metal in an acidic solution and then
   (b) treating the noble metal surface of step (a) with an aqueous salt solution, whereby slightly soluble noble metal salts or a mixture of noble metal salts of different solubility products are formed on the noble metal surface, which salts have grown directly on the base material;
   wherein noble metal ions are released from said noble metal surface and replenished from the noble metal surface of the base material during sterilization to produce a self-regulating and maintenance-free sterilization system.

2. The process as claimed in claim 1, characterized in that the noble metal is copper, silver or gold.

3. The process as claimed in claim 1, characterized in that the base material is a solid body made of noble metal or an alloy comprising noble metal, a noble metal wire, noble metal wool, knitted noble metal fabric or woven noble metal fabric, a support coated with noble metal or a mixed woven fabric or mixed knitted fabric made of noble metal, or a noble metal powder, a shaped body comprising noble metal powder, or a coating comprising noble metal powder.

4. The process as claimed in claim 3, characterized in that the fabric is made of noble metal together with synthetic and/or carbon fibers.

5. The process as claimed in claim 1, characterized in that the acidic solution has a pH less than 1 and/or comprises water and/or the acidic solution comprises oxidizing inorganic or organic acids and/or mixtures of non-oxidizing acids with water-soluble oxidizing agents.

6. The process as claimed in claim 1, characterized in that the acidic solution comprises acids which contain nitrogen in oxidation state +5, sulfur in oxidation state +VI, the halides chlorine, bromine and iodine in oxidation state +5 or +7, boron in oxidation state +3, manganese in oxidation state +7 and/or oxygen in oxidation state −1 or −2.

7. The process as claimed in claim 1, characterized in that the salt solution comprises hydroxide, carbonate, chloride, bromide, permanganate, chlorate, perchlorate, percarbonate, persulfate, iodate, periodate, perborate, oxalate, bromate and/or perbromate ions and/or anions of pharmacologically active noble metal compounds.

8. The process as claimed in claim 1, characterized in that the aqueous salt solution is weakly acidic (pH>4) to alkaline (pH approximately 11), and/or the aqueous salt solution and/or the acidic solution is 0.1% by weight to saturated or concentrated, respectively, and/or the aqueous solution is free from ammonium compounds or sulfide ions.

9. The process as claimed in claim 8, characterized in that the aqueous salt solution is neutral or alkaline.

10. The process as claimed in claim 1, characterized in that the base material, after the oxidation and before the treatment with the salt solution, is quenched with water.

11. The process as claimed in one of the preceding claims, characterized in that the oxidation of the noble metal surface in the acidic solution and/or the quenching with water and/or the treatment with the salt solution is performed in a temperature range between 10° C. and 130° C.

12. The process as claimed in claim 11, characterized in that the treatment with the salt solution is performed in a temperature range below 80° C.

* * * * *